United States Patent [19]

Lescure

[11] 4,293,412

[45] Oct. 6, 1981

[54] ANAEROBIC FERMENTER-DECANTER FOR THE PURIFICATION OF RESIDUAL WATER FROM SUGAR REFINERIES, WITH RECOVERY OF COMBUSTIBLE METHANE

[75] Inventor: Jean-Pierre Lescure, Mons-En-Baroeul, France

[73] Assignee: Syndicat National des Fabricants de Sucre de France, Paris, France

[21] Appl. No.: 114,426

[22] Filed: Jan. 22, 1980

[30] Foreign Application Priority Data

Jan. 24, 1979 [FR] France ................................ 79 01775

[51] Int. Cl.³ .............................................. C02F 3/28
[52] U.S. Cl. .................................... 210/179; 210/180; 210/539
[58] Field of Search ............... 210/170, 174, 180, 188, 210/218, 539, DIG. 9

[56] References Cited

U.S. PATENT DOCUMENTS

| | | | |
|---|---|---|---|
| 2,195,408 | 4/1940 | Downes | 210/179 X |
| 2,605,220 | 7/1952 | Logan | 210/539 X |
| 2,891,675 | 6/1959 | Kaplon | 210/539 |
| 3,239,067 | 3/1966 | Hikes et al. | 210/539 X |
| 3,981,803 | 9/1976 | Coulthard | 210/180 X |

*Primary Examiner*—Thomas G. Wyse
*Attorney, Agent, or Firm*—Young & Thompson

[57] ABSTRACT

An anaerobic fermenter-decanter for the purification of residual water from the sugar industry, with recovery of methane, consists of a tank with inclined walls, with a central agitator on a vertical shaft. A flexible cover anchored by its periphery to the walls of the tank and totally submerged forms a collecting pocket for the fermentation gases. The water to be purified is introduced, after being heated to about 35°, towards the bottom of the tank near the agitator. A metal collecting bell with submerged edges and with the shaft of the agitator passing axially through it is connected by its edges to a central opening of the cover. The purification yields may exceed 90%.

4 Claims, 4 Drawing Figures

ANAEROBIC FERMENTER-DECANTER FOR THE PURIFICATION OF RESIDUAL WATER FROM SUGAR REFINERIES, WITH RECOVERY OF COMBUSTIBLE METHANE

BACKGROUND OF THE INVENTION

1. Field of the Invention

The invention relates to a fermenter-decanter intended for the purification of residual waters, particularly from sugar refineries, with recovery of the fermentation gases which consist for the most part of combustible methane.

2. Description of the Prior Art

Conventional purification by storing the residual water from sugar refineries in static water, this residual water containing various sugars which are destroyed by fermentation during the storage in the static water, requires very large tanks, causes the release of disagreeable odours into the environment, does not permit precise control of the effective purification level and, finally, means that the energy contained in the sugar products is left to disperse into the ambient medium.

The inventor and his fellow-workers have made studies in the purification of residual water by fermentation under the effect of mesophilic anaerobic micro-organisms (i.e. those which are active in a temperature range around 35° C.), the results of this type of fermentation being mainly methane and carbon dioxide, the latter being largely held in a carbonate combination, whilst the methane which is released constitutes a useful fuel. In fact, fermentation occurs in two stages; in the first stage, acidifying micro-organisms convert the sugars into organic acids, whilst strictly anaerobic mesophilic micro-organisms decompose the acids into methane, carbon dioxide and water.

The inventor's studies were based on laboratory tests, then tests on pilot fermenters. A first pilot plant, comprising a 90 m$^3$ tank, at the Escaudoeuvres sugar refinery, was followed by a second with a 1580 m$^3$ tank at the sugar refinery of Vauciennes. A description of the work and the plants will be found in the journal Sucrerie Francaise: "La depollution des eaux", by J. P. Lescure and P. Bourlet, March 1977, pages 103-109; "Nouvelles perspectives pour le traitement des eaux en sucrerie; la fermentation méthanique mésophile", P. Devillers, J. P. Lescure and P. Bourlet, April 1977, pages 173-183; and "Traitement des eaux residuaires par fermentation méthanique mésophile", J. P. Lescure, P. Bourlet, March 1978, pages 107-114. In the plants described, fermentation took place at about 35° C. by the passage of the affluent into a heater, from which this affluent was carried along piping to the bottom and near the centre of the tank, where it was mixed up by a rotary agitator. A cover made of reinforced butyl rubber was anchored by its periphery and submerged in the tank and covered the fermentation zone so as to form a collection pocket for the methane released, which was evacuated via tubing fixed to the upper part of the cover pocket. This arrangement, which resulted in rapid completion of the fermentation process, nevertheless had some disadvantages which affected the safety of use and the reliability of the installation. In fact, the cover was not tensioned and partially emerged from the water. The agitation of the residual water below the cover was transmitted to the cover, which then became subject to premature cracking. Leakages through the cover, through the beginnings of cracks, created a danger of explosions or fire in the pocket inflated by the gas.

SUMMARY OF THE INVENTION

To remedy these disadvantages, the invention provides an anaerobic fermenter-decanter intended for the purification of residual water, especially from the sugar industry, with recovery of the fermentation gases, which consist for the most part of combustible methane and comprising a tank excavated in the ground with a fluid-tight skin, in the form of a truncated pyramid with walls widening upwards and a substantially flat bottom and adapted to be substantially filled with residual water to be purified, towards the centre of the tank a rotary agitator with a vertical shaft having an impeller near the bottom, a flexible cover extending in the central zone of the tank, anchored by its periphery substantially halfway up the walls and forming a pocket for collecting the fermentation gases, with a tube for the evacuation of the fermentation gases at the top and pipes for the intake of residual water passing through a heater and opening out near the impeller, wherein a collecting bell made of metal, with submerged edges and having the shaft of the agitator passing axially therethrough, is connected by its edges to a central opening of the cover, the latter being tensioned between its central opening and the peripheral anchoring points.

With the metal collecting bell alone emerging from the tank, the fermentation gases are not present in a substantial quantity, in the undispersed state in the residual water, except in the bell and the evacuation tubing. Thus, the risk of leakages of combustible gas is virtually eliminated. The cover, being supported between the bell and the anchoring points, is not susceptible to any great movements; moreover, the movements of the cover are suppressed by the presence of water on both its surfaces. The risk of cracking is therefore greatly reduced.

Preferably, the bell comprises a collecting chamber which is open at the bottom and laterally bounded by inner and outer edges, the latter forming a connection with the central opening of the cover, whilst the inner edge surrounds the agitator axis, defining a sealed cavity with a lower flange. Thus, gas leaks along the agitator axis are reduced.

Preferably, the outer edge of the bell is surrounded by an annular spout open at the top, with a horizontal peripheral rim forming an overflow lip and a channel for the evacuation of purified residual water. As the level of residual water in the tank is determined by the overflow lip over which the purified residual water being evacuated through the channel flows, the depth of immersion of the edges of the bell is maintained constant.

According to a preferred arrangement, the periphery of the cover is braced by rods passing through lap-joints and fixed by tensioning means to the anchoring points, the latter being fixed in a frame formed by beams extending horizontally substantially halfway up the tank. This ensures satisfactory rigidity of the cover's edges without subjecting the cover to excessive local stresses. The beam-type frame ensures good performance of the anchoring points, thanks to its weight and structure, without the need to bury these anchoring points in the underlying ground, piercing the fluidtight skin.

DETAILED DESCRIPTION OF THE INVENTION

Figure 1:
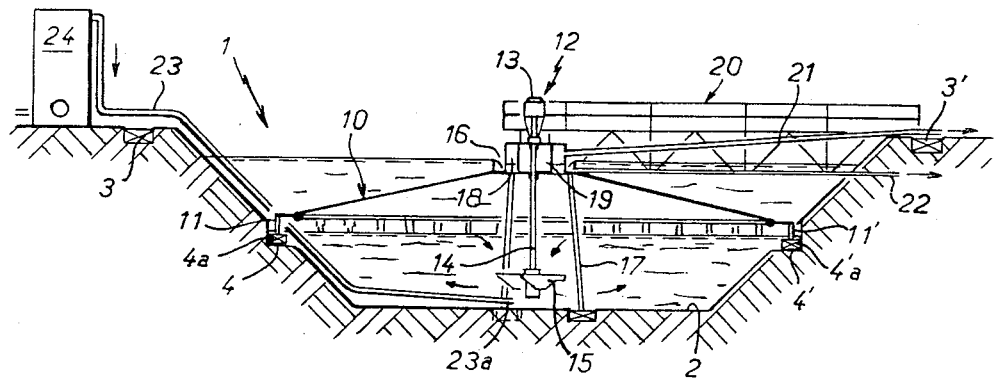
FIG. 1 shows a general sectional view of a fermenter-decanter according to the invention.

According to the preferred embodiment of the invention shown in FIG. 1, a fermenter-decanter comprises, excavated in the ground, a tank 1 in the general form of a straight truncated pyramid with a square base, with edges opening outwardly in the upward direction and inclined at about 45°. A fluidtight skin 2, formed in known manner by assembling plastics sheets, is fixed at its periphery by being buried in trenches 3, 3' and is weighted with blocks of masonry. Halfway up the inclined edges are provided horizontal set-offs 4, 4' to which the fluidtight skin is adapted in form. On these set-offs 4, 4' are placed concrete beams 4a, 4'a which form a frame in which are fixed piles or anchoring points 11, 11' for a submerged flexible cover 10 in the form of a pyramid with a square base. At the top of the cover 10, this cover is connected to a collecting bell 12 which partially emerges from the water and which has in its centre a motor 13 for a rotary agitator with a vertical shaft 14 ending near the bottom of the tank with a helical impeller 15. The bell 12 is held to the bottom of the tank by a tripod support 17 and is connected to the periphery of the tank by a platform 20 which forms a support for a tube 21 for the evacuation of fermentation gases which comes out of the annular chamber 18, opening towards the bottom of the bell 12 and for a channel 22 for evacuating the purified waste water, said channel starting from the peripheral spout 16. The waste water to be purified, or affluent, is introduced into the tank 1 through piping 23 the end 23a of which opens out near the bottom of the tank, in the vicinity of the impeller 15; this is after it has passed through a heater 24 intended to bring the temperature of the affluent to about 35°, as this temperature promotes the activity of mesophilic anaerobic micro-organisms.

Figure 2:
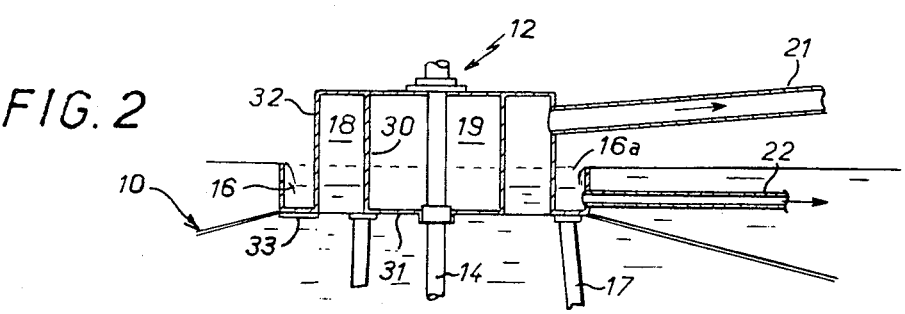
FIG. 2 shows a collecting bell in more detail.

The bell 12 with the shaft 14 of the agitator passing vertically through it is more clearly shown in FIG. 2. The bell consists of an annular chamber 18 bounded by inner and outer cylindrical walls 30 and 32, respectively, which are coaxial with the shaft 14 and this chamber is open at the bottom. The inner wall 30 has a flange 31 on its lower part so as to define a sealed cavity 19 through which the shaft 14 passes. Surrounding the outer wall 30, the annular spout 16 is provided with a peripheral rim 16a which forms an overflow lip for the purified waste water or effluent, so as to define the level in the tank whilst ensuring that the walls 30 and 32 are permanently partly submerged. The cover 10 is clamped between the base of the spout 16 and a circular crown 33 which terminates the tripod support 17. It will be appreciated that the fermentation gases formed below the cover 10 collect in the chamber 18 to be evacuated through the tubing 21 without penetrating to an appreciable extent into the cavity 19, as the submerged flange 31 obstructs the passage of the gases.

Figure 3:
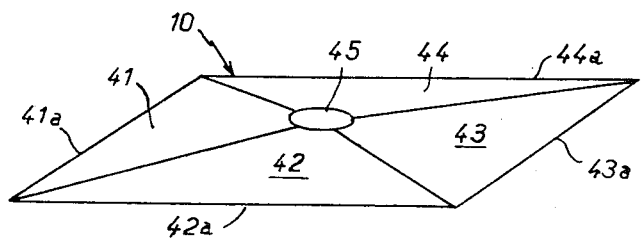
FIG. 3 is a schematic perspective view of a collecting cover.

As can be seen from FIG. 3, the cover 10 is made up of four triangular sections 41, 42, 43 and 44 converging towards the top circular connecting aperture 45 with the collecting bell. The bases 41a, 42a, 43a and 44a of the sections are reinforced by rods to form a square.

Figure 4:
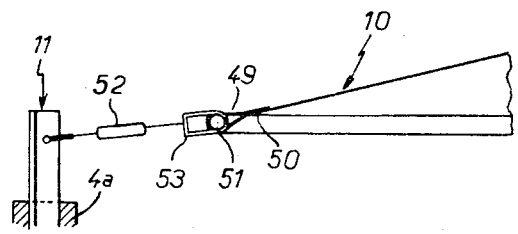
FIG. 4 is a detailed view of the arrangement for peripherally anchoring the cover.

FIG. 4 shows, in more detail, how the edges of the cover 10 are stiffened and anchored. The cover edge forms a lap-joint 49, by the bending and fastening of the border 50 over the cover 10. A rod (metal tube) 51 is passed through the lap-joint 49. The anchoring on the pile 11 fixed in the beam 4a is obtained by means of a tensioning member 52 of the nature of a long nut with a reversed thread engaging with two threaded rods, the rod located nearest the cover 10 ending in a yoke 53 which fits over the rod 51. Controlled tightening of the tensioning nuts makes it possible to tension the cover uniformly over its entire periphery, whilst the tensile stresses of the tensioning members 52 are transmitted uniformly to the cover via the reinforcing rod 51 and lap-joint 49.

In one embodiment, the tank, with a fluidtight skin of reinforced polyvinyl chloride, had an opening, at ground level, with sides 22 meters long and with a depth of 5 meters, with walls inclined at 45°. The agitator was a helical mixer (S E M H M 2500) with variable speeds, permitting circulation flow rates of 3000 to 17600 m$^3$/h, at operating cycles of between 3.2 and 22 revolutions per minute, whilst the motor had a power of 10 h.p.

Nutrient nitrogen- or phosphorus-containing products may optionally be added to the affluent introduced under the cover, so as to obtain a C/N/P equilibrium of ~300/5/1. The pH is maintained constant by the addition of lime and scum (CaCO$_3$) from the clarification of juices. After fermentation, the waste water passes round the periphery of the cover in order to be clarified by decantation in the part of the tank located above the cover (decantation surface area approximately 400 m$^2$). The slurry is evacuated discontinuously by means of a submerged pump, whilst the clarified effluent passes into the spout and is evacuated as fast as the affluent is introduced.

For the test results, the following abbreviations are used:

COT total organic carbon content;

DCO chemical oxygen requirement;

DBO$_5$ biological oxygen requirement, up to day 5.

| Purification Results | | | | | |
|---|---|---|---|---|---|
| Week | Average flow rate m$^3$/h | DCO taken Kg/day | Charge by volume kg DCO/m$^3$/day | Gas production m$^3$/day | Yield % |
| 43 | 27.0 | 2430 | 3.04 | 490 | 83 |
| 45 | 37.6 | 5022 | 6.28 | 960 | 83 |
| 47 | 31.9 | 3926 | 4.91 | 550 | 88 |
| 48 | ~30 | 3000 | 3.75 | 518 | 70 |
| 49 | 18.3 | 2020 | 2.53 | 700 | 77 |
| 50 | 19.5 | 2915 | 3.64 | 706 | 97 |

| Analysis | minimum | mean | maximum |
|---|---|---|---|
| Affluent | | | |
| COT mg/l (C) | 1145 | 1956 | 2280 |
| DCO mg/l (O) | — | 5896 | 6900 |
| DBO$_5$ mg/l (O) | — | 3983 | 4920 |
| Kjeldahl nitrogen mg/l (N) | 37 | 49.7 | 62 |
| Total Phosphorus ng/l (P) | 6.3 | 8.4 | 9.9 |
| Total sulphur | 0.4 | 6.5 | 19.3 |
| Effluent | | | |
| COT mg/l | 62 | 414 | 807 |
| DCO mg/l | 340 | 1107 | 2400 |
| DBO$_5$ mg/l | 95 | 720 | 1600 |
| N Kjeldahl mg/l | 14 | 36.7 | 41 |

|  | -continued | | |
|---|---|---|---|
| P total mg/l | 2.5 | 4.3 | 6.7 |
| S total mg/l | 0 | 3.0 | 7.5 |
| Gas % | | | |
| $CO_2$ | 9.96 | 12.30 | 15.8 |
| $H_2$ | traces | 0.22 | 0.42 |
| $O_2$ | 0.8 | 1.11 | 1.76 |
| $N_2$ | 3.18 | 3.95 | 6.14 |
| $CH_4$ | 80.00 | 82.41 | 85.95 |

By recovering 700 m$^3$/day of gas containing 82.5% methane, i.e. 420 kg of methane per day, one has calorific energy of about 5000 therms, i.e. approximately 5800 kW/h, whilst the purification of waste water attains a valuable level.

Obviously, from the calorific energy recoverable, one must deduct the energy required to heat the affluent, but the balance sheet still remains positive and can be improved by passing the effluent and affluent in counterflow through a heat exchanger, so that the losses of heating energy are limited to the losses on the surface of the tank. Moreover, in absolute terms, these losses increase more slowly than the capacity of the tank.

Although the fermenter-decanter described above has been produced within the framework of the sugar refining industry, which produce large quantities of fermentable effluent requiring purification before it is disposed of in the environment, it is plain that there is no obligatory connection between the structures described and the origin of the fermentable effluent and consequently the fermenter-decanter can be used for the treatment of effluent from any origin, provided that this effluent is capable of anaerobic fermentation under the effect of specific micro-organisms, with methane as the end product.

In fact, methane is the chief end product of all reducing degradation of organic matter and anaerobic micro-organisms select themselves under conditions in which their activity is optimum, these conditions including the nutrient medium (effluent which has optionally been adjusted), the temperature and an adequate dispersion of the micro-organisms in the effluent. From this point of view, the arrangements used in this fermenter-decanter are generally suitable and lend themselves to the particular adjustments required. Moreover, the structure of the fully submerged collecting pocket is suitable for collecting any combustible gas formed within an agitated liquid filling a tank under conditions of safety and reliability, for a relatively low installation cost, whatever the formation process of the combustible gas. However, the formation process of the combustible gas is specifically fermentation.

It is obvious that the invention is not limited to the examples described, but covers all variants.

I claim:

1. An anaerobic fermenter-decanter for digesting and clarifying sludge from sugar manufacturing and refining plants and for recovering fermentation gases, said anaerobic fermenter-decanter comprising an upwardly opening inverted truncated pyramid shape tank having a substantially flat bottom wall and a fluidtight skin covering the sidewalls and the bottom wall thereof, an intake pipe passing through a heater and delivering heated sludge to the bottom of said tank adjacent an impeller carried by a vertical shaft of a rotary agitator, a flexible cover anchored at its periphery midway along the height of the side walls of the tank and extending inwardly to a central opening, said cover being tensioned between the central opening and its peripheral anchoring, a metal collecting bell having free edges adapted to be immersed in the sludge and attached at the central opening of the cover, whereby fermentation gas produced during digestion is collected at the center of the cover, an evacuation tube for removing the fermentation gas from the center of the cover, the peripheral edges of the cover and the adjacent side walls of the tank defining between them a marginal peripheral space for the flow of digested sludge upwardly to a decantation area disposed in the upper part of the tank above the cover so that the cover is entirely immersed in said tank, means for removing the digested sludge from the upper part of the tank, and means for removing clarified liquid from the upper part of the tank.

2. A fermenter-decanter according to claim 1, wherein said collecting bell comprises a downwardly opening annular collecting chamber defined between inner and outer walls, said cover being attached to the collecting bell at said outer wall, the inner wall of the collecting chamber surrounding the agitator axis and defining with a lower flange a sealed cavity.

3. A fermenter-decanter according to claim 2, wherein said means for removing clarified liquid from the upper part of the tank comprises gutter means surrounding the outer wall of the collecting bell and forming an overflow lip, and an evacuation channel for carrying the clarified liquid, said gutter means determining the level of liquid in the upper part of the tank and thereby insuring that the cover is constantly immersed.

4. A fermenter-decanter according to claim 1, wherein the periphery of the cover has a hem with peripherally extending rods, and tensioning members attached between the rods and horizontally extending beams for tensioning the cover.

* * * * *